United States Patent [19]

Drouen

[11] Patent Number: 5,203,992

[45] Date of Patent: Apr. 20, 1993

[54] APPARATUS FOR OPTIMIZING THE LIQUID CHROMATOGRAPHIC SEPARATION OF A SAMPLE

[75] Inventor: Antonius Drouen, Waldbronn, Fed. Rep. of Germany

[73] Assignee: Hewlett-Packard Company, Palo Alto, Calif.

[21] Appl. No.: 844,901

[22] Filed: Mar. 2, 1992

Related U.S. Application Data

[63] Continuation of Ser. No. 507,606, Apr. 10, 1990, abandoned.

[30] Foreign Application Priority Data

Jun. 23, 1989 [EP] European Pat. Off. ........ 89111420.9

[51] Int. Cl.$^5$ .............................................. B01D 15/08
[52] U.S. Cl. .................... 210/198.2; 210/656
[58] Field of Search ...................... 210/656, 659, 96.1, 210/101, 198.2; 422/70; 436/161

[56] References Cited

U.S. PATENT DOCUMENTS

| | | | |
|---|---|---|---|
| 3,701,609 | 10/1972 | Bailey | 210/198.2 |
| 4,063,077 | 12/1977 | Wright | 210/198.2 |
| 4,066,879 | 1/1978 | Leaver | 210/198.2 |
| 4,116,046 | 9/1978 | Stein | 210/198.2 |
| 4,237,422 | 12/1980 | Lenhardt | 210/656 |
| 4,357,668 | 11/1982 | Schwartz | 210/198.2 |
| 4,364,263 | 12/1982 | Sankoorikal | 210/198.2 |
| 4,579,663 | 4/1986 | Poile | 210/198.2 |
| 4,592,842 | 6/1986 | Tomlinson | 210/198.2 |
| 4,595,495 | 6/1986 | Yotam | 210/198.2 |
| 4,595,496 | 6/1986 | Carson | 210/198.2 |
| 4,719,017 | 1/1988 | Uchino | 210/656 |
| 4,762,617 | 8/1988 | Stevens | 210/656 |
| 4,802,981 | 2/1989 | Kenney | 210/656 |
| 4,886,590 | 12/1989 | Tittle | 204/406 |
| 4,927,532 | 5/1990 | Pospisil | 210/198.2 |
| 4,969,993 | 11/1990 | Nash | 210/143 |

OTHER PUBLICATIONS

Annino, R. & Villalobos, R., "A Computer Aided Optimization Program Including Stationary Phase Selection and Optimized Analysis Conditions", *Advances in Instrumentation*, 1986, 41, 383–402.

Snyder, L. R., et al., "High-performance liquid chromatographic method-development using computer simulation", *TrAC*, 1987, 6(5), 106–111.

Berridge, J. C., "Using a Microprocessor in high performance liquid chromatography", *Microprocessors and Microsystems*, 1983, 7(1), 19–23.

Drouen, A. C. J. H., et al., "An Improved Optimization Procedure for the Selection of Mixed Mobile Phases in Reversed Phase Liquid chromatography", *Chromatographia*, 1982, 16, 48–52.

Primary Examiner—Ernest G. Therkorn

[57] ABSTRACT

An apparatus for optimizing the liquid chromatographic separation of a sample comprises means for performing liquid chromatographic separations at selectable values of an optimization parameter, such as the composition of the mobile phase. Based upon measured chromatographic data of the sample and upon a mathematical model, the retention behavior of the sample as a function of the optimization parameter is derived by data processing means and displayed on a display means. An input means permits the chromatographer to select from the displayed retention behavior a desired value of the optimization parameter. In response to such a selection, the resulting chromatogram for this value is calculated and displayed. By means of the displayed retention behavior and the corresponding chromatograms, the chromatographer can quickly locate a value of the optimization parameter for which optimal results can be expected. Then, a chromatographic separation of the sample is performed with the selected value. The chromatographic data obtained in that separation are used to refine the mathematical model from which a new retention behavior is derived. The process is iterated until a desired optimum is achieved.

13 Claims, 2 Drawing Sheets

APPARATUS FOR OPTIMIZING THE LIQUID CHROMATOGRAPHIC SEPARATION OF A SAMPLE

This is a continuation of application Ser. No. 507,606, filed Apr. 10, 1990, now abandoned.

BACKGROUND OF THE INVENTION

This invention relates to an apparatus and a method for optimizing the separation of a liquid chromatographic sample and, more specifically, to an apparatus and method for optimizing such separation with respect to an optimization parameter.

In the analytical method of liquid chromatography, a sample to be analyzed is injected together with a suitable solvent (mobile phase) into a separation column, typically under very high pressure. The various components of the sample interact differently with the column material and the solvent such that the components elute from the column at different times. The substances leaving the column are subsequently detected by a detector such as, for example, a photometric detector. The time between the injection of a sample and the detection of a specific component is called the retention time for that component. The results of chromatographic separations are displayed as a plot of detector signal versus time, commonly known in the art as a chromatogram. A chromatogram typically comprises a plurality of peaks, wherein each peak corresponds to a certain component of the sample to be analyzed. The area of the peak is to some degree characteristic of the amount of the respective component present in the sample.

In order to ensure a reliable qualitative and quantitative analysis of the sample, it is necessary that the chromatogram has a good overall resolution, which is characterized by distinct, narrow peaks for different components. In chromatograms with bad overall resolution, it is frequently not possible to so recognize that adjacent peaks actually correspond to different sample components. Likewise, it may not be possible to derive meaningful quantitative values for the amounts of these components present. It is known that the overall resolution of a chromatogram for a specific sample depends upon the composition of the mobile phase and that an improvement of this resolution can be achieved by varying this composition as, for example, by blending several solvents in a certain ratio.

Thus, much effort has been directed to the development of mobile phase compositions resulting in optimal liquid chromatographic separations. One method for the selection of the optimum mobile phase composition in liquid chromatography is known from A. C. J. H. Drouen, et al., "An Improved Optimization Procedure for the Selection of Mixed Mobile Phases in Reversed Phase Liquid Chromatography", Cromatorapia, Vol. 16, pages 48-52, which is incorporated herein by reference. This method is an iterative optimization approach wherein some chromatograms of a sample to be examined are measured at different solvent compositions and, based upon the measured chromatograms, a so-called retention model is calculated which describes the chromatographic capacity factor as a function of solvent composition for the various components of the sample. Using this retention model, an overall resolution value is derived for each possible solvent composition, whereby the overall resolution value is a measure of the quality of the chromatographic separation for the respective solvent compositions. The chromatographer then initiates a new chromatographic separation with a solvent composition having a resolution value at or near the maximum of the optimal separation. The new experimental data thus obtained are used to refine the retention model, from which a new resolution value function is derived. The procedure can be repeated until the optimum mobile phase has been found.

However, this known optimization procedures is not satisfactory in all respects. Depending upon the definition of the overall resolution value, the optimization procedure may lead to different results, that is, to different solvent compositions which are regarded as optimal. Furthermore, the resolution value may not be sufficiently discriminating between different chromatographic separations; the resolution values associated with different separations are identical or very close to each other so that it is difficult to predict where optimal conditions are to be searched. One way to overcome these difficulties is to define overall resolution in a way which will provide better discrimination. However, even such redefined resolution is not satisfactory for all separation problems. Consequently, differing optimization criteria are sometimes employed, leading to a complication of the optimization procedure. Furthermore, this known method only offers limited flexibility. If, for example, the chromatographer is interested in an optimal separation of one of the sample's components, the known method, which is based on determining an overall resolution, is of limited use.

SUMMARY OF THE INVENTION

This invention provides an apparatus and a method for optimizing liquid chrmatographic separations which ensures more flexibility to the chromatographer in determining optimal conditions for a separation problem. The method is relatively uncomplicated and ensures a fast determination of such optimal conditions. The apparatus comprises means for performing liquid chromatographic separation of a sample comprising a plurality of components, data processing means for deriving retention behavior of the components as a function of an optimization parameter and for deriving chromatograms corresponding to selectable values of an optimization parameter, and display means for displaying the derived retention behavior as a function of the optimization parameter and for displaying derived chromatograms corresponding to selected values of the optimization parameter.

DESCRIPTION OF THE PREFERRED EMBODIMENTS

Figure 1:
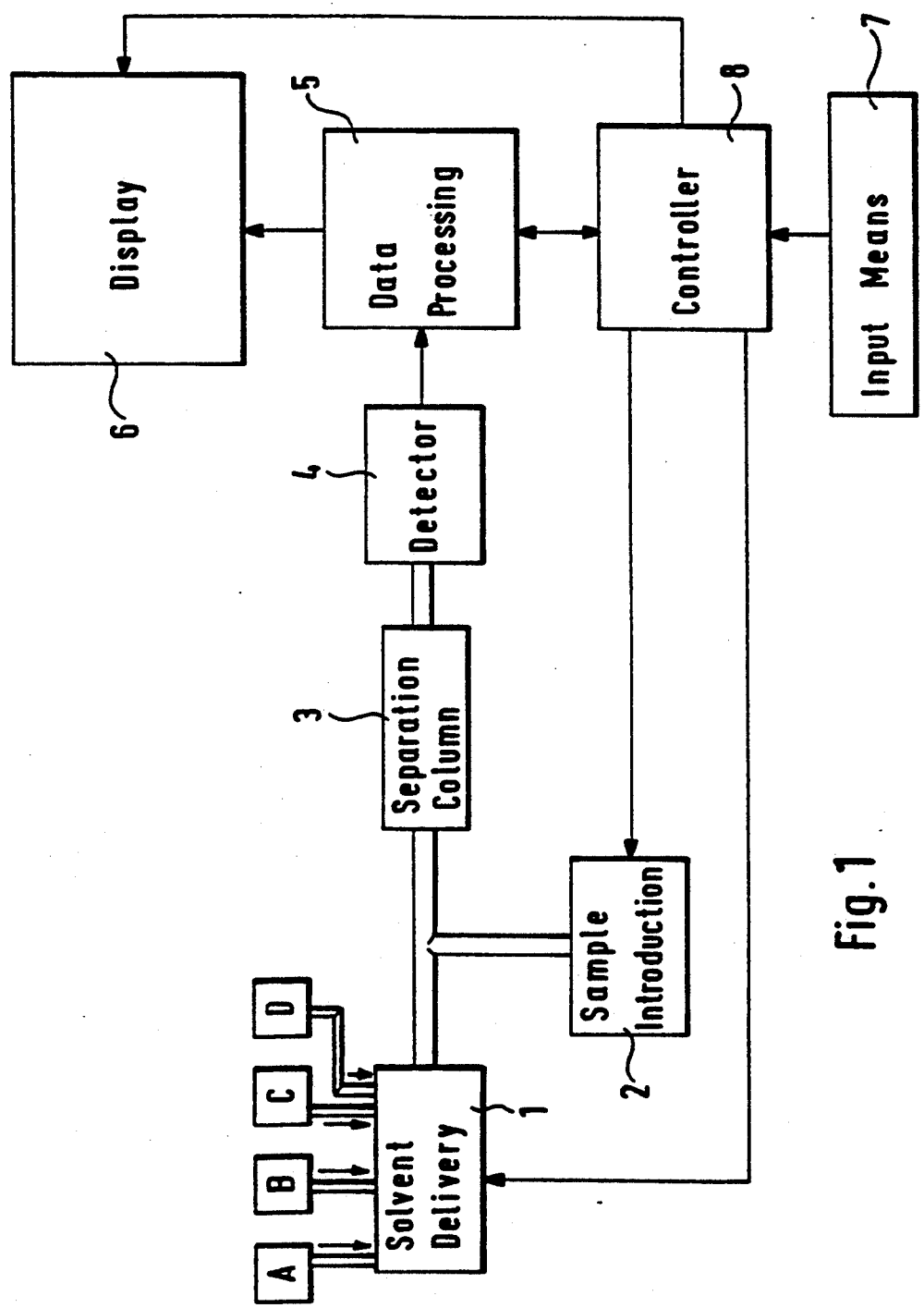
FIG. 1 schematically depicts an apparatus according to the invention for optimizing liquid chromatographic separations.

It is preferred that a liquid chromatographic apparatus comprise means to calculate and to display the retention behavior of the sample components by reference to an optimization parameter, for example by reference to the composition of the mobile phase. The calculations are based on a theoretical model as well as on experimentally—derived data. The retention model displayed by processing mean on display means gives the user a first indication of the optimization parameter optimal conditions. The user can then select from the displayed retention model by means of a marker, such as a movable cursor, the optimization parameter or those parameters which appear to give optimum conditions. When the user has made such a selection, the corresponding chromatograms are calculated and displayed. The user can thus directly determine whether the resulting chromatograms are suited for his particular separation problem. For example, the user can see at once if all peaks are clearly separated from each other at a specific optimization parameter or if two or more peaks coincide. If the user is only interested in a separation of a few of the sample components, the invention permits the user to select the optimization parameter which gives the best resolution for just these peaks of interest. Furthermore, the user may select an optimization parameter for which the components of interest are separated in a less than optimal manner, but which parameter gives a short analysis time; shorter, for example, than for the separation which has the greatest overall separation of the peaks. Accordingly the user can design an optimum between peak separation and analysis time.

In a preferred embodiment, the optimization procedure starts with the recording of a chromatogram for at least two limiting values of an optimization parameter, such as the composition of the mobile phase. Then, the retention for the individual components of the sample is derived using the measured limiting values and a mathematical model for the retention. A plot of retention versus optimization parameter is then displayed. Once the user has selected new parameter conditions from the displayed retention behavior and the corresponding displayed chromatograms, an actual chromatographic separation is performed with these selected parameter conditions, such as a certain solvent composition, and the experimental data obtained in that chromatographic run are used to refine the mathematical model for the retention. This procedure can be repeated several times until satisfactory chromatograms result. It is understood that the expression "retention behavior" describes the time sequence of the elution of the sample components from the separation column. According to a preferred embodiment, this may be the retention time, but other modes of display would also be possible such as a logarithmic representation of retention time. When the retention time is displayed on the display means, the user can directly determine the analysis times for the chromatographic separations.

The invention provides great flexibility in selecting those chromatographic conditions which are considered optimal for the respective separation problem. In the prior art, the optimization is based on a single quality factor, and an undue simplification of the whole optimization problem is introduced, which may lead to unsatisfactory optimization results. In contrast thereto, the apparatus of this invention provides a complete overview of the entire optimization problem, namely of the retention behavior across the entire range of the optimization parameter, and additionally derives and displays chromatograms selected from the displayed retention behavior. In this manner, the invention offers the possibility of direct visual comparison of "magnitudes" which give a much better description of the quality of the separation than the quality factors of the prior art, namely the chromatograms themselves.

According to an embodiment of the invention, the display of the retention behavior not only comprises the display of the variation of the retention as a function of the optimization parameter, but also comprises the display of a calculated band width for the individual sample components corresponding to the widths of the peaks in the chromatograms. Thus, it can be determined from the displayed retention behavior where sample components overlap.

In another embodiment, a calculated separation quality curve can be displayed simultaneously with the retention behavior and the chromatograms, thus providing an additional tool for selecting optimal conditions. It would also be possible to display several separation quality curves.

For example, FIG. 1 shows an apparatus according to the invention for performing liquid chromatographic separations and for optimizing such separations. The apparatus comprises a solvent delivery system (1) to which several solvent reservoirs (A, B, C, and D) are connected. The solvents may be of any type used in liquid chromatography, such as water, methanol, acetonitrile, tetrahydrofuran. The solvent delivery system provides predetermined mixtures of the solvents (A, B, C, and D) according to the control signals from a controller (8) and delivers at its outlet a high pressure stream of these mixtures. It is understood that the invention is not limited to four solvents, but that any number of solvent reservoirs may be connected to the solvent delivery system.

A sample introduction means (2) can be operated to inject predetermined amounts of sample into the solvent stream from the solvent delivery system (1). The sample is then transported under high pressure into the separation column (3) in which the various components are separated from each other and elute from the column (3) at different times. A detector (4) connected to the outlet of the column (3) provides output signals indicative of the components in the sample. The detector may be of any typed used in liquid chromatography, such as photometric detector, florescence detector, conductivity detector, electrochemical detector, or any other type suitable for detecting the components of interest.

The output signal of the detector (4) is supplied to a data processing means (5) wherein a chromatogram is derived from the detector signals. Processing means which can be employed in the practice of this invention consist of any computing device capable of compiling and executing instructions. The chromatogram, i.e., a graphical representation of detector output signal versus retention time, can be displayed on a display means (6) such as the screen of a cathode ray tube. The data processing means (5) is not only capable of deriving a chromatogram from the detector output signals but is also capable of calculating a chromatogram based on certain input parameters. Such calculated chromatograms can also be displayed on the display means (6). Furthermore, calculated curves showing the retention behavior for different components of the sample as a function of the solvent composition as well as curves describing the chromatographic resolution as a function of solvent composition can be displayed. In order to perform these tasks, a color graphics terminal may be used to better distinguish the various curves from each other by the use of a different color for each curve.

An input means (7) connected to the controller (8), which in turn is connected to the display (6), gives a user the possibility to interact with the chromatographic systems by to enter commands which the system is to execute or by requesting information from the system which is then displayed on the display means (6). The input means (7) may be, for example, a keyboard by which the user may type in commands and control one or several cursors on the display (6). It is understood that instead of a keyboard or in addition to it any other input device can be used, such as a computer mouse, a trackball or a contact screen wherein the user touches certain areas on the screen to input certain commands to the controller (8).

A typical optimization procedure is now described by reference to FIG. 2, which is a graphical representation appearing on the display means (6) during the optimization procedure. The graphical representation comprises three main blocks (20, 21, 22) wherein different kinds of information used by the chromatographer for the optimization process are displayed.

In block (20) is displayed a derived retention model for the specific separation in the form of a plot of retention versus solvent composition for the different components of the sample. The example shown relates to the separation of a sample of nine anti-epileptic drugs. The nine shaded bands labelled with the letters (a) to (i) correspond to these nine components of the sample. The horizontal axis of the plot is the retention time, expressed, for example, in minutes, and the vertical axis is the solvent composition. In the example shown, the solvent composition varies between a first limiting value of 60% water/40% methanol (upper end of vertical scale) and a second limiting value of 80% water/20% tetrahydrofuran (lower end of vertical scale). The values between these two limiting values represent the possible mixing ratios between these two limiting values. This can be illustrated by considering two solvent containers, one containing a mixture of 60% water/40% methanol, and the other containing a mixture of 80% water/20% tetrahydrofuran. The possible mixtures of the contents of these two containers provide the values on the vertical scale of block (20).

For example, the horizontal lines (30, 31, and 32) correspond to the three solvent compositions:

a) 65.4% water ($H_2O$); 5.4% tetrahydrofuran (THF); 29.3% methanol (MeOH);

b) 66.3% $H_2O$; 6.3% THF; 27.4% MeOH; and c) 67.5% $H_2O$; 7.5% THF; 24.9% MeOH.

The solvent composition between the two limiting values can be described mathematically by a parameter (X) varying within a certain interval.

In the retention model shown in block (20), the retention times for the components (a–i) of the sample are displayed as a function of solvent composition, along with the bandwidths (w) for the components as a function of solvent composition. Thus, a cross section along a horizontal line in the retention model of block (20), such as lines (30), (31), or (32), corresponds to a chromatogram, i.e., a display of the chromatographic peaks as a function of retention time. In block (21) are displayed the three chromatograms resulting from horizontal cross sections along the lines (30), (31), (32), respectively. The positions of the lines can be selected by the user via the input means (7). Preferably, the lines can be moved in response to user control between the limiting values like a cursor, for example via corresponding keys on a keyboard or via a computer mouse, such that the momentary position of the cursor line is displayed on the screen (6), respectively.

The chromatogram corresponding to the momentary position of the cursor line is displayed in block (21). In the present example, the chromatograms corresponding to cursor lines (30), (31), (32) are displayed in the upper, middle, and lower third of block (21), respectively. The data corresponding to the displayed chromatograms are derived by the data processing means (5) from the data representing the retention model displayed in block 20. The displayed chromatograms show peaks labelled with the letters (a) to (i) according to the components in the sample as shown in the retention model in block (20). The chromatographer can thus directly perceive the chromatograms which would result at a certain solvent composition for the displayed retention model so that he can quickly decide which solvent composition would provide the best separation.

In block (22) is displayed a separation quality factor for the chromatograms as a function of solvent composition. The separation quality factor is a measure of how well the individual components in the sample are separated from each other. Separation quality factor is a measure of the overall resolution of the chromatogram and may defined in numerous ways. Block (22) displays the resolution of the worst-separated peak pair in a chromatogram, whereby resolution is defined as the quotient of the difference in retention times of these peaks and the sum of widths of the peaks. The vertical axis in the display of block (22) corresponds to the solvent composition and is identical to the vertical axis of the display of block (20). The horizontal axis indicates the magnitude of the quality factor.

In the right half of block (22) is displayed a second separation quality factor curve, wherein the quality factor is defined differently than in the left half. The quality factor therein is proportional to the product of all resolutions of adjacent peaks in the chromatogram, in accordance with equation (2) of the Drouen article which has been incorporated by reference.

As in the left half of block (22), the vertical axis corresponds to the solvent composition and the horizontal axis (starting from the middle of the block) indicates the magnitude of the quality factor. The horizontal cursor lines (30), (31), and (32), which have been described in connection with block (20) extend beyond block (20) into block (22) to guide the eye of the user in reading the separation quality factor for any solvent composition selected with the help of the line cursors (30), (31), or (32).

As can be seen from block (22), the separation quality factor curves in the left and in the right half differ from each other. In particular, the maxima of these curves are at different locations, i.e., at different solvent compositions. The user may choose which separation quality curve he wants to employ in consideration for selecting the solvent composition that he regards as optimal. Also shown in block (22) is a shaded band (40) which belongs to the separation quality curve in the left half and which serves to define a range for a certain minimum separation quality. The separation quality values at the intersection of the horizontal line cursors (30, 31, 32) with the separation quality curves may be displayed on the screen.

Figure 2:
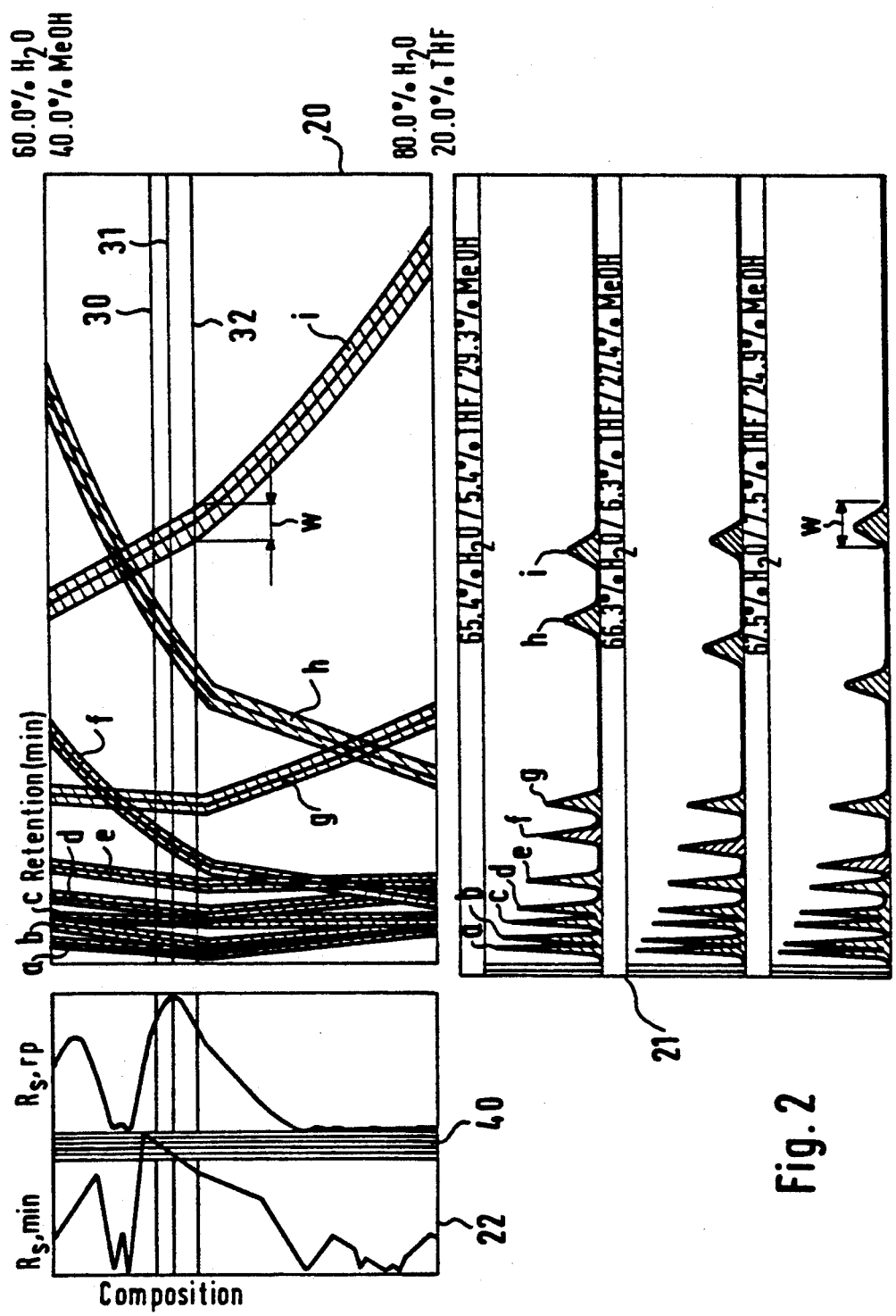
FIG. 2 illustrates a typical display of calculated retention data and chromatograms displayed during the optimization procedure.

In summary, the display according to FIG. 2 shows the user in block (22) the calculated retention model, i.e. the dependence of the retention time on solvent composition. The display also permits the user to mark certain solvent compositions for which the resulting chromatogram is then calculated and displayed in block (21). Blocks (20) and (21) are aligned so that he user can easily associate the peaks of displayed chromatograms with the bands shown in the retention model. Also displayed are one or more separation quality curves which are aligned with the retention model block (20) such that the user directly gets information about a separation quality value for a selected solvent composition. The bands in the retention model and the associated peaks in the chromatograms are colored in the same way, respectively, so that identification of the various components in the retention model display and in the display of chromatograms is facilitated. Instead of using different colors for the different sample components, it is also possible to use different shadings.

Thus, the graphical representations appearing on the display means (6) during the optimization process have been explained. It will now be explained how the displayed data are obtained and, more particularly, how the retention model displayed in block 20 is derived.

In a first step of the optimization procedure, the limiting or starting conditions are fixed. When the optimization parameter is the solvent composition as shown in FIG. 2, two limiting solvent compositions are determined between which the optimization parameter (X) can vary. In the present example, these limiting conditions are: 60% H$_2$O/40% MeOH, and 80% H$_2$O/20% THF. The limiting conditions can be established in different ways. One possible choice, corresponding to FIG. 2, is to select two limiting solvent compositions such that the analysis times for the sample of interest, i.e., the retention times of the last sample components eluting from the separation column, respectively, are substantially equal.

When the limiting conditions have been fixed and the chromatograms resulting at these conditions have been recorded, the first retention model is calculated by the data processing means (5) and then displayed by the display means (6) in the block (20).

In one embodiment of the invention, the calculation of the retention model is performed as follows. First, it is assumed as a theoretical model that the natural logarithm of the chromatographic capacity factor ($k_i$) for the sample component (i) varies linearly with the optimization parameter (X), such as the solvent composition. Thus equation (1) applies:

$$ln\ (k_i) = (a \cdot X) + b \qquad (1)$$

wherein (a) and (b) are constants. This model has been found to be an adequate description of the actual retention behavior, yet it is mathematically simple. For the capacity factor of the ith sample component the well-known relation of equation (2) applies:

$$t_{ri} = (1 + k_i) \cdot t_o \qquad (2)$$

where ($t_o$) is unretained time or void time of the column. Based upon this theoretical model, a linear interpolation between the experimentally determined limiting conditions is performed. That means that in a plot of (ln k) versus (X) the limiting conditions are connected by a straight line in order to obtain the values between the limiting values. The retention times for the individual sample components are calculated from the thus interpolated capacity factors using equation (2).

The data thus obtained characterize the variation of the retention times for the individual sample components as a function of solvent composition and correspond to the center lines of the shaded bands displayed in block (20). The widths (w) of the bands shown in block (20) are determined, according to this particular example, by the relationship, $w = 4 \cdot \delta_i$, whereby ($\delta_i$) is the standard deviation of a Gaussian peak and is given by the formula:

$$\delta_i = t_{ri}(N)^{-\frac{1}{2}} \qquad (3)$$

wherein ($t_{ri}$) is the retention time of the ith sample component, and (N) is the plate number of the separation column which can be entered into the data processing means by the user. The chromatographic peaks (a)–(h) displayed in block (21) are Gaussian peaks having a standard deviation ($\delta_i$), which means that the full width of these peaks at a fraction of 0.607 of their total height is equal to ($2\delta_i$). It is understood that the invention is not limited to Gaussian peaks, but that other peak shapes are possible and that the width of the peaks may be defined in a different manner.

All data required for block (20) have been calculated and can be displayed. The separation quality factor(s) are calculated and displayed in block (22). The user now has an overview of the retention model in the entire range of solvent compositions and determines where optimum conditions can be expected. The display of the quality factor provides the user with an additional instrument to decide with which solvent compositions he could obtain the best results. When the user has positioned the horizontal cursors (30), (31), and (32) at certain solvent compositions, the resulting chromatograms are calculated by the data processing means (5) and displayed in block (21). The use of several cursors has the advantage that several chromatograms can be directly compared. The calculation and display of chromatograms requires only a very short time period. It occurs almost instantaneously with the positioning of the cursor at a certain solvent compositions so that the user can quickly scan all possible chromatograms.

In the left half of block (20), it can be seen that the quality curve has a sharp maximum above the cursor line (30) with a steep slope towards the upper end of block (22). Consequently, the quality of the separation would change drastically for optimization parameters in that area. It can also be seen that below the cursor line (30) the variation of the quality value is comparatively smooth. Thus, it is advisable to select a parameter value from this area. The invention thus also has the advantage that a kind of "robustness information" is provided to the user in the form of information about the degree of the change (gradient) of the quality as a function of the optimization parameter.

When the user has determined which of the chromatograms best fits his chromatographic needs, he selects this chromatogram by entering a corresponding command via the input means (7). Then, the controller (5) initiates a chromatographic separation of the sample with a solvent composition which corresponds to the selected chromatogram. For example, if the user has decided from FIG. 2 that the chromatogram in the mean third of block (21) (according to the position of cursor (31) in block (20)) is the best one, he presses a certain key to select that chromatogram and to start a chromatographic run with that solvent composition. This chromatographic run produces new experimental data which are stored in the data processing means and which are used to calculate a refined retention model.

The new retention behavior model is derived according to the same principle as explained above in connection with the first model, namely by linear interpolation of the natural logarithm of the retention factor ($k_i$) as a function of the solvent composition (X) in accordance with equation (1). Thus, in a plot of ln ($k_i$) as a function of (X), the experimentally determined points are piecewise connected by straight lines. The widths of the bands or the new retention model are calculated in accordance with equation (3). The new retention model is displayed in block (20), where it replaces the first retention model. Also calculated and displayed in block (22) are the separation quality factors. The user can position the cursors (30, 31, 32) at any desired place along the vertical axis of block (20), causing the corresponding chromatogram to be calculated and displayed in block (21). The user views and compares the displayed chromatograms and selects the one which appears optimal.

Then, a new chromatographic separation of the sample is carried out with the solvent composition corresponding to the selected chromatogram. The new experimental data are used to refine this retention model. Again, the user selects an optimal chromatogram, and the process starts anew. The above-described steps are repeated several times until the retention model no longer changes substantially, that is, until the "true" retention model for the sample has been found. Typically, good results can be achieved after 3 to 5 runs.

Thus, an iterative, interactive optimization process is provided which is fast and yet very flexible, as it enables the user to use his own judgement of what to consider as optimal conditions.

Instead of being Gaussian in shape, the calculated chromatographic peaks might have another profile, which might even be asymmetric. It is also understood that the widths of the bands displayed in block (20) are not limited to the (4δ) width according to equation (3). The width of the bands might be equal to, for example, the width of the corresponding chromatographic peaks at half of their maximum. Furthermore, various modifications to the specific display mode shown in FIG. 2 are possible. For example, if the retention for the sample components is displayed as a function of an optimization parameter and the chromatograms corresponding to selectable parameters can be displayed.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the the invention's true spirit and scope.

What is claimed is:

1. An apparatus for optimizing the liquid chromatographic separation of a sample comprising a plurality of components with respect to an optimization parameter, comprising:
    means for performing liquid chromatographic separations at selected values of the optimization parameter;
    data processing means programmed to:
        derive retention behavior of each component as a function of the optimization parameter; and
        derive chromatograms corresponding to selectable values of the optimization parameter; and
    display means for displaying the derived retention behavior as a function of the optimization parameter and for displaying the derived chromatograms.

2. The apparatus of claim 1, further comprising controller means for initiating a further liquid chromatographic separation of the sample at a selected value of the optimization parameter, said further separation being initiated in response to the selection of the specific value from the values of the optimization parameter displayed on the display means.

3. The apparatus of claim 2, wherein the data processing means is programmed to derive retention behavior as a function of the optimization parameter using the retention behavior measured in the further liquid chromatographic separation.

4. The apparatus of claim 1, further comprising marking means displayed and movable on the display means for selecting certain values of the optimization parameter from the display of the retention behavior, wherein the positioning of the marking means at a certain value of the optimization parameter causes the corresponding chromatogram to be derived by the data processing means and to be displayed by the display means.

5. The apparatus of claim 1, wherein the data processing means is programmed to derive, from the retention behavior, at least one separation quality factor for the displayed values of the optimization parameter, and wherein the display means display a graphical representation of the separation quality factor simultaneously with the display of the retention behavior.

6. The apparatus of claim 1 wherein retention behavior comprises retention time for at least one sample component.

7. The apparatus of claim 6, wherein the display of the retention behavior comprises a graphical representation of retention time of at least one sample component versus the optimization parameter.

8. The apparatus of claim 6 wherein retention behavior further comprises the width of at least one chromatographic peak.

9. The apparatus of claim 8, comprising means for deriving the width of at least one chromatographic peak as a function of retention time.

10. The apparatus of claim 1, wherein the data processing means derives retention behavior according to:

$$ln(k_i) = (a \cdot X) + b$$

wherein $k_i$ is the chromatographic capacity factor, X is the optimization parameter, and a and b are constants, and wherein derived retention behavior are obtained by interpolating between measured retention behavior.

11. The apparatus of claim 1, wherein means for performing the liquid chromatographic separation comprises a mobile phase having known composition.

12. The apparatus of claim 11, wherein the optimization parameter is the relative composition of the mobile phase.

13. The apparatus of claim 1, wherein the selectable values are between the selected values.

* * * * *